United States Patent
Lee et al.

(10) Patent No.: US 9,176,060 B2
(45) Date of Patent: Nov. 3, 2015

(54) APPARATUS AND METHODS TO MEASURE OPTICAL DENSITY

(75) Inventors: Harry Lee, Malden, MA (US); Kevin Shao-Kwan Lee, Cambridge, MA (US)

(73) Assignee: Pharyx, Inc., Woburn, MA (US)

( * ) Notice: Subject to any disclaimer, the term of this patent is extended or adjusted under 35 U.S.C. 154(b) by 680 days.

(21) Appl. No.: 13/442,783

(22) Filed: Apr. 9, 2012

(65) Prior Publication Data

US 2013/0194575 A1    Aug. 1, 2013

Related U.S. Application Data

(60) Provisional application No. 61/590,850, filed on Jan. 26, 2012.

(51) Int. Cl.
*G01N 21/00* (2006.01)
*G01N 21/59* (2006.01)
*G01N 21/03* (2006.01)
*G01N 1/20* (2006.01)

(52) U.S. Cl.
CPC ............ *G01N 21/59* (2013.01); *G01N 21/0303* (2013.01); *G01N 2001/2057* (2013.01)

(58) Field of Classification Search
CPC ............... G01N 9/20; G01N 9/32; G01F 1/74
USPC .......................... 356/246, 436, 441, 432, 433
See application file for complete search history.

(56) References Cited

U.S. PATENT DOCUMENTS

| | | | |
|---|---|---|---|
| 4,762,798 A | 8/1988 | Deutsch | |
| 4,786,171 A | 11/1988 | LeFebre et al. | |
| 5,044,755 A | 9/1991 | Landa et al. | |
| 5,268,736 A | 12/1993 | Prather | |
| 5,303,036 A | 4/1994 | McLachlan et al. | |
| 7,507,579 B2 * | 3/2009 | Boccazzi et al. | 435/297.5 |
| 7,539,593 B2 * | 5/2009 | Machacek | 702/127 |
| 7,826,050 B2 | 11/2010 | DiFoggio et al. | |
| 2004/0135089 A1 | 7/2004 | Manz et al. | |
| 2005/0156124 A1 | 7/2005 | Tobimatsu | |
| 2010/0118414 A1 * | 5/2010 | Bolis | 359/666 |

OTHER PUBLICATIONS

Teruyuki Fujita and Kazuko Nunomura, "New Turbidimetric Device for Measuring Cell Concentrations in Thick Microbial Suspensions", Appl. Microbiol. 1968, 16(2):212.
K.S. Lee, R.J. Ram, "Plastic—PDMS bonding for high pressure hydrolytically stable active microfluidics", Lab Chip, 2009, 9, 1618-1624, DOI: 10.1039/b820924c.

* cited by examiner

*Primary Examiner* — Gregory J Toatley
*Assistant Examiner* — Iyabo S Alli
(74) *Attorney, Agent, or Firm* — May Ming Wu (57) ABSTRACT

The present invention provides apparatus and methods for measuring the optical density of a fluid by measuring the light transmission through a reconfigurable optical path. The optical path is reconfigured by the deflection of an elastic membrane wherein the optical path length through the fluid is determined by the position of the membrane relative to a fixed surface. The optical density can be determined from two measurements with different optical path lengths through the fluid.

13 Claims, 7 Drawing Sheets

APPARATUS AND METHODS TO MEASURE OPTICAL DENSITY

RELATED APPLICATIONS

This application claims priority from U.S. Provisional Application 61/590,850, entitled "Apparatus and methods to measure optical density", filed Jan. 26, 2012, the content of which is hereby incorporated by reference in its entirety.

STATEMENT REGARDING FEDERALLY SPONSORED RESEARCH OR DEVELOPMENT

This work was funded under federal grant number DE-FG02-08ER85207.

TECHNICAL FIELD

The field of the invention relates to measurement of optical properties of a fluid or particles suspended in a fluid.

BACKGROUND OF THE INVENTION

All referenced patents and applications and publications are incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply.

The measurement of the optical density of a fluid that contains optical absorbers or scatters can yield valuable information about the sample, such as the quantity of the optical absorber or quantity of scatterers. Typically, optical density is measured by removing a sample of the fluid, placing it in a sample container, possibly diluting the sample, and measuring the optical transmission through the sample using instruments such as a spectrophotometer. In addition, the optical transmission through a blank, or reference sample is measured and optical density is then computed as $-10*\log 10(Tsample/Tblank)$. Measurement of transmission through a blank or reference sample is intended to cancel out sources of transmission reduction that are not intrinsic to the sample.

It is, however, desirable to perform optical density measurements online and in-situ without removing the sample, when sample removal is inconvenient, risky, or impossible. Examples include measurement of optical density in miniature, or microfluidic devices where there is not enough fluid to sample, including microfluidic bioreactors where it is desirable to monitor the cell density, in stirred tank bioreactors where sample removal increases contamination risk, or at the bottom of the ocean where sample retrieval is difficult.

In-situ optical density measurements are subject to errors because reference sample measurement is difficult. One method is to perform a reference measurement at the beginning of the experiment allowing changes in the optical density from a starting point to be recorded. This method suffers from error due to variations in the intensity of the light source and fouling of optical surfaces which cause a reduction in transmission that is not related to the optical density of the fluid. Another approach is to perform optical density measurements using two different path lengths. Using this approach, the transmission through the shorter path length serves as the reference for the transmission through the longer path length and the computed optical density refers to the optical density of the fluid in the difference between the path lengths. There are multiple methods for implementing multiple path lengths. One is to use two fixed, independent optical paths through the fluid. A problem with this approach is an error is introduced if the optical fouling on the surfaces of the different optical paths is not the same. Another is to introduce a transparent material into the optical path, as taught in U.S. Pat. No. 7,826,050, after a first measurement, thereby reducing the proportion of the optical path through the fluid, and then taking a reference measurement. A problem with this approach is that the reference measurement with the transparent material has additional optical surfaces that can be fouled when compared to the optical path without the transparent material. Yet another approach is to physically move the optical surfaces to change the optical path length as taught in U.S. Pat. No. 4,786,171, U.S. Pat. No. 5,168,367, U.S. Pat. No. 5,268,736, and U.S. Pat. No. 5,303,036. This method reduces the chances of error, however it is the most mechanically complicated to implement, requiring a sliding seal and mechanical means to change the optical path length.

Another source of interference that is more difficult to remove is, light scattering from gas bubbles which also reduce transmission in a way not related to the optical density of the fluid. Gas bubbles are common in systems where gas is a reactant and is supplied to the vessel in small gas bubbles. In addition, for certain biological or chemical processes, gas bubbles can be generated by the reaction.

Thus, there remains a considerable need for devices and methods to measure optical density in-situ that minimize errors due to optical fouling and gas bubbles.

SUMMARY OF INVENTION

The present invention relates to determining the optical density of a fluid by measuring the light transmission through a reconfigurable optical path. The optical path is reconfigured by the deflection of a portion of an elastic membrane wherein the optical path length through the fluid is determined by the position of the membrane relative to a surface. The optical density is estimated from measurements with different optical path lengths through the fluid.

Among the many different possibilities contemplated, the optical path passes through transparent materials but may be redirected by a reflection. It is further contemplated that the surfaces and elastic membrane may be substantially planar or in cross section form a closed contour as is the case for a cylindrical geometry. It is further contemplated that the optical path passes through one or more apertures. It is further contemplated that two optical paths can be configured by deflecting the elastic membrane to contact different surfaces. When the membrane is deflected to be in contact with a first surface, the fluid is nominally excluded from the optical path and when the membrane is deflected to be in contact with a second surface, the fluid is included from the optical path.

In one aspect of the present invention, deflection of deformable portions of the elastic membrane can be accomplished by establishing a pressure difference between the two sides of the membrane. In another aspect of the present invention, the fluid to be characterized is in an enclosed surface bounded by at least two deformable portions of the elastic membrane.

Among many possibilities contemplated, one application of the invention is for online monitoring of the optical density of a cell culture or microbial fermentation.

In one aspect, the present invention relates to an apparatus for measuring the optical density of a fluid comprising: a light source; a light detector; an elastic membrane; a first deformable portion of the elastic membrane with a first side fluidically isolated from a second side that is in contact with the fluid; a first surface facing the second side of the first deformable portion of the elastic membrane with at least a portion of the first surface in contact with the fluid; and a reconfigurable optical path from the light source to the light detector that passes through the fluid, wherein the optical path length through the fluid is determined by the position of the first deformable portion of the elastic membrane relative to the first surface.

In another aspect, the present invention relates to a method to measure optical density of a fluid comprising the steps of: configuring a first optical path length through the fluid defined by a first surface and the second side of a deformable portion of an elastic membrane, wherein the deformable portion of the elastic membrane is deflected in a first position; activating a light source and light detector; measuring the quantity of light transmission, T1, along an optical path from the light source to the light detector that includes the first optical path length through the fluid; configuring a second optical path length through the fluid defined by a the first surface and the second side of the deformable portion of the elastic membrane, wherein the deformable portion of the elastic membrane is deflected in a second position; wherein the second optical path length is less than the first optical path length; and measuring the quantity of light transmission, T2, along the optical path from the light source to the light detector that includes the second optical path length through the fluid.

Various features and aspects of the present invention will become more apparent from the following detailed description of preferred embodiments of the invention, along with the accompanying drawings in which like numerals represent like components.

BRIEF DESCRIPTION OF THE DRAWING

The embodiments of the present invention will now be described by reference to the following figures, and in which.

DETAILED DESCRIPTION OF THE DRAWING

A substantially planar embodiment of the invention is shown in FIGS. 1-9.

Figure 1:
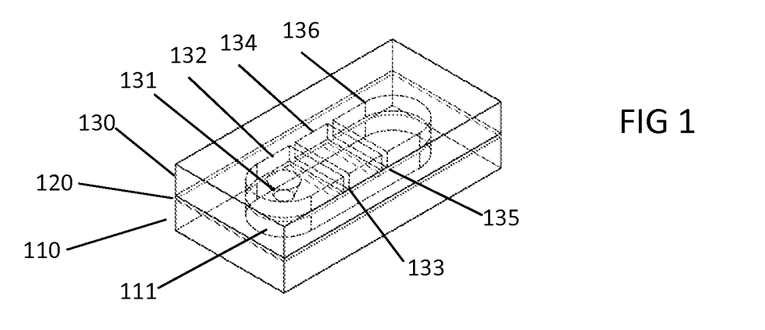
FIG. 1 is an isometric view of a substantially planar embodiment.

FIG. 1 shows an isometric view of the embodiment comprising a first layer 110 with a pocket 111 where the fluid to be measured was introduced, a second layer 120, and a third layer 130 with two pockets 132 and 136, and an optional third pocket 134. One pocket, 132 had a raised island of material 131 through which the optical path passed.

Referring in more detail to FIG. 1, the three layers 110, 120, and 130 were bonded together using the method described in ["Plastic-PDMS bonding for high pressure hydrolytically stable active microfluidics", Lab Chip, 2009, 9, 1618-1624, DOI: 10.1039/b820924c], but may be bonded together utilizing other methods known in the art including the use of silicone pressure sensitive adhesives, or other adhesives, covalent chemical surface bonds, or other bonding methods. The second layer 120 was an elastic elastomer membrane. The elastomer membrane was purposely not bonded to the island 131, and was optionally bonded to the region 133 between pockets 132 and 134, and the region 135 between pockets 134 and 136. The island 131 served as a surface of a first rigid material upon which the membrane could contact to define a first optical path. The pockets 132, 134, and 136 provided space for the membrane to deflect upwards to accommodate the displacement of fluid introduced into pocket 111. Bonding of the three layers 110, 120, and 130 fluidically isolated the upper side of the elastic membrane from the bottom side of the elastic membrane.

In further detail, still referring to FIG. 1, the first layer 110 of the preferred embodiment had a length of 3 inches but can have a length of 0.1 inches to 10 inches; had a width of 2 inches but can have a width of 0.1 inches to 10 inches; and had a thickness of 0.125 inches but can have a thickness of 0.01 inches to 3 inches. The second layer 120 of the preferred embodiment had a length of 3 inches but can be 0.1 inches to 10 inches; had a width of 2 but can have a width of 0.1 inches to 10 inches; and had a thickness of 0.003 inches but can have a thickness of 0.0001 inches to 0.5 inches. The third layer 130 of the preferred embodiment had a length of 3 inches but can have a length of 0.1 inches to 10 inches; had a width of 2 inches but can have a width of 0.1 inches to 10 inches; had a thickness of 0.093 inches but can have a thickness of 0.01 inches to 3 inches. The pocket 111 of the preferred embodiment had a length of approximately 1.5 inches but can have a length of 0.01 inches to 10 inches; had a width of approximately 1 inch but can have a width of 0.01 inches to 10 inches; and had a depth of 0.06 inches but can have a depth of 0.001 inches to 3 inches. The pockets 132 and 136 of the preferred embodiment had a length of approximately 0.75 inches but can have a length of 0.1 inches to 10 inches; had a width of approximately 0.75 inches but can have a width of 0.1 inches to 10 inches; and had a depth of 0.06 inches but can have a depth of 0.001 inches to 3 inches. The optional pocket 134 of one embodiment was implemented and had a length of approximately 0.75 inches but can have a length of 0.1 inches to 10 inches; had a width of approximately 0.3 inches, but can have a width of 0.1 inches to 10 inches; and had a depth of 0.06 inches but can have a depth of 0.001 inches to 3 inches.

The island 131 of the preferred embodiment was circular in shape, but can be any shape, preferably smooth with an optional draft. The diameter of the island of the preferred embodiment was 0.2 inches but can have a diameter of 0.01 inches to 3 inches. The height of the island 131 had a height measured from the bottom of pocket 132 of 0.06 inches but can have a height of 0 inches to 3 inches. In particular it is to be noted that a height of 0 inches corresponds to not having island 131. In general the shapes of the elements can be any shape, not necessarily similar to rectangular prisms. The shapes should be selected to avoid sharp convex features that would create high stress points if the membrane deflects into the pocket.

In still more detail, still referring to FIG. 1, the first layer 110 of the preferred embodiment was made of polycarbonate but can be made of another rigid material such as acrylic, cyclic polyolefin copolymer, or other thermoplastic, or other rigid material. The second layer 120 of the preferred embodiment was made of polydimethylsiloxane, but can be made of polyurethane, rubber, or another elastomeric material to form an elastomer membrane. The third layer 130 of the preferred embodiment was made of polycarbonate but can be made of another rigid material such as acrylic, cyclic polyolefin copolymer, or other thermoplastic, or other rigid material. The pocket were fabricated by machining, but can be fabricated using other means known in the art including but not limited to molding, or embossing. The elastomer membrane was fabricated by spin coating but can be fabricated by other means known in the art including but not limited to casting, spraying, gravure coating, metering rod coating, or knife coating.

For the purposes of this description, a fluid to be characterized was introduced into the region defined by the pocket 111 and the membrane 120. The fluid was introduced by injecting a quantity of fluid through a septa connected to a channel (not shown) connected to the pocket 111, but can be introduced by other means known to one of ordinary skill in the art such as by fabricating an inlet channel and outlet channel in layer 110 that connects the pocket 111 to an inlet hole and an outlet hole. Fluid can then be introduced into the inlet hole and channel with air displaced out of the outlet channel and outlet hole. After introducing the fluid, the inlet and outlet holes may be sealed to isolate the pocket 111 from the external environment.

Figure 2:
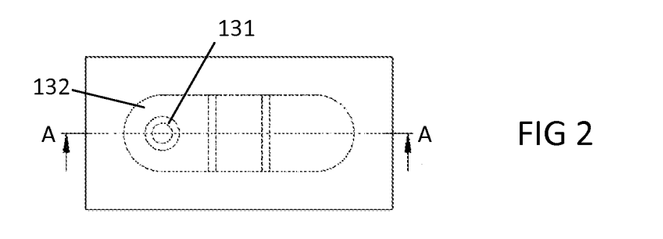
FIG. 2 is a top view of the embodiment shown in FIG. 1.
Figure 3:
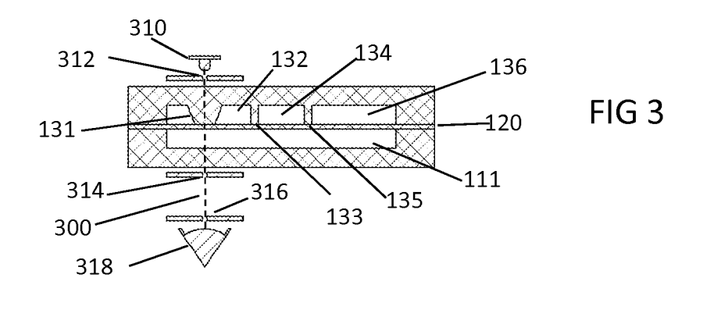
FIG. 3 is a section view along the line A-A in FIG. 2. with the addition of an embodiment of optical components including a light source, 3 apertures, and a detector.

FIG. 3 shows a cross-sectional view of the planar embodiment along the line A-A shown in FIG. 2. The pockets 132, 134, 136, and island 131 can be more easily visualized in this cross section. Also shown are embodiments of optical elements used to measure optical transmission and also a dashed line 300 showing the optical path from a light source 310 through a first aperture 312, through the island 131 of rigid material, through the membrane 120 of elastic material, through the fluid in pocket 111, through the rigid material of layer 110, through a second aperture 314, through a third aperture 316, and to a detector 318.

For measurement of optical density where transmission loss is due to optical scattering, it is a preferred embodiment to minimize the numerical aperture, or angle of light rays from the optical axis entering the detector to maintain a linear relationship between optical density and scattering particle concentration. That apertures 314 and 316 reduce the numerical aperture of the light entering the detector should be recognized by those of ordinary skill in the art. By aligning two small holes along the optical axis, spaced a distance apart, the only light that can pass through both apertures has a small angular spread defined by the inverse tangent of the radius of the holes divided by the distance between the holes. While two apertures are shown, one skilled in the art would recognize that more or less apertures are also possible.

Figure 4:
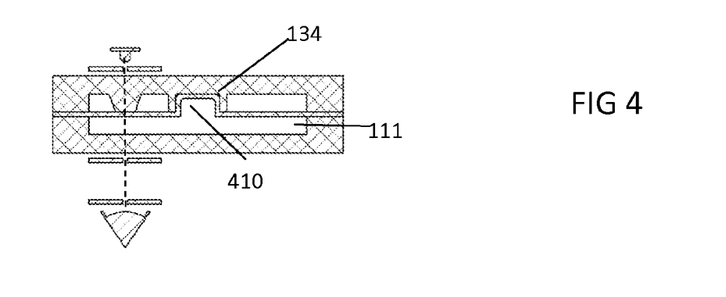
FIG. 4 shows a modification of FIG. 3 where the embodiment is configured to remove bubbles.

To aid in the removal of bubbles, vacuum was applied to the optional pocket 134 through a hole (not shown) that connected to pocket 134 and a channel placing pocket 134 in fluid communication with a vacuum source. Other methods to apply a vacuum to the pocket 134 would be obvious to one skilled in the art. With the application of a vacuum, the membrane inside the perimeter of pocket 134 was deflected into the pocket as shown in FIG. 4. Bubbles introduced to or formed in the fluid that traverse the pocket 111 were preferentially captured by the region 410 under the membrane area that was deflected into pocket 134. While vacuum was applied to pocket 134, bubble absorption occurred.

Figure 5:
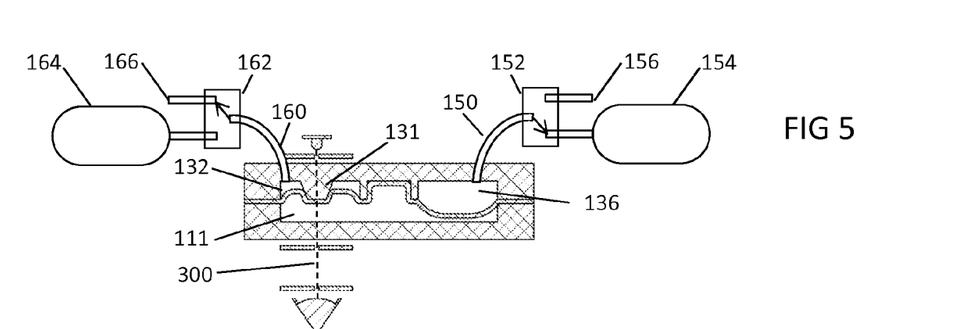
FIG. 5 shows a modification of FIG. 4 where the embodiment is configured to measure a sample transmission.

In FIG. 5, the planar embodiment was configured in the sample configuration to measure the optical transmission through the fluid. A first 3-way valve 152 was configured to place a source 154 of pressurized gas in fluid communication with pocket 136 through a conduit 150. A second 3-way valve 162 was configured to place a vent 166 in fluid communication with pocket 132 through a conduit 160. The pressure of the gas from source 154 was sufficient to deflect the membrane area under pocket 136 down into pocket 111, which displaced the fluid to preferentially move under pocket 132 and force the membrane area under pocket 132 to contact the island 131 of rigid material and deflect into pocket 132. In this configuration, the optical path 300 between the surface of the island 131 and bottom surface of pocket 111 maximally passed through the fluid in pocket 111. A liquid rather than a gas could also be introduced into pocket 136 to deflect the membrane 120 instead of introducing a pressurized gas into pocket 136. More generally, the pressurized liquid or gas used to deflect the portion of membrane 120 under pocket 136 can be described by the term deflecting fluid. Alternatively, a vacuum could be applied to pocket 132 to achieve the configuration shown in FIG. 5.

Figure 6:
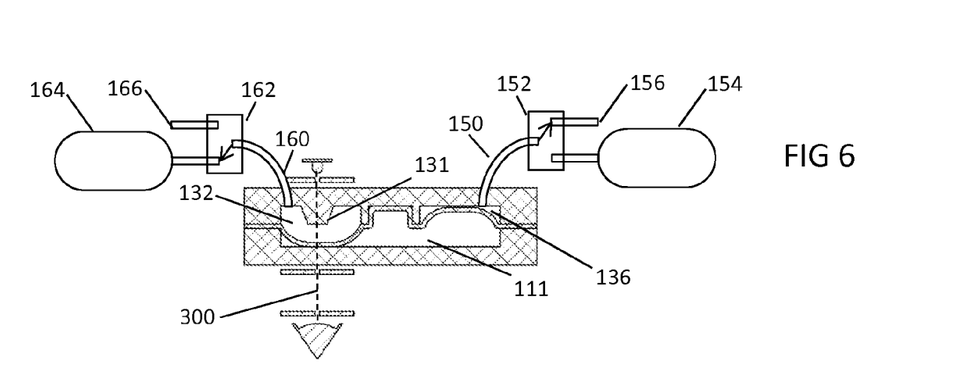
FIG. 6 shows a modification of FIG. 4 where the embodiment is configured to measure a reference transmission.

In FIG. 6, the planar embodiment was configured in the reference configuration to measure the optical transmission without the fluid. The first 3-way valve 152 was configured to place a vent 156 in fluid communication with pocket 136 through the conduit 150. The second 3-way valve 162 was configured to place a source 164 of pressurized gas in fluid communication with pocket 132 through a conduit 160. The pressure of the gas in source 164 was sufficient to deflect the membrane area under pocket 132 such that the membrane 120 made contact with the bottom surface of the pocket 111 and the fluid was displaced toward and preferentially moved under pocket 136 where it deflected the membrane area under pocket 136 into pocket 136. In this configuration, the optical path 300 between the surface of the island 131 and the bottom surface of pocket 111 did not pass through the fluid in pocket 111. Rather than applying a gas pressure to pocket 132, applying a vacuum to pocket 136 could also achieve the configuration shown in FIG. 6. It is also contemplated that a liquid could be introduced into pocket 132 instead of introducing a pressurized gas into pocket 132 to deflect the membrane 120 such that it contacts the bottom surface of pocket 111. In general, the substance introduced to pocket 132 to deflect the membrane will be referred to as a reference fluid. Using a liquid with similar refractive index as the fluid in pocket 111 has the additional advantage that all optical interfaces will be the same. More generally, the optical transmission of the fluid in pocket 111 in the sample configuration can be referenced with the optical transmission of the fluid (liquid or gas) in pocket 132 in the reference configuration. When the optical properties of the reference fluid are not the same as the fluid in pocket 111, a correction factor to account for different reflections at the interfaces between the materials is necessary for precise optical density measurements. This correction factor is an adjustment to the reference transmission and may be captured in the optical density calculation as an additive constant term where (optical density)=−10*log 10(Ts/Tr)+(correction factor).

In more detail, in the sample configuration the optical interfaces which can have reflections if the interfacing materials have different indicies of refraction are between the island 131 and the elastic membrane 120 with reflection coefficient R1; between the elastic membrane and the fluid with reflection coefficient R2; and between the fluid and the bottom of pocket 111 with reflection coefficient R3. In the reference configuration, the interfaces and reflection coefficients are between the island and the reference fluid with reflection coefficient R4; the reference fluid and the elastic membrane 120 with reflection coefficient R5; and the elastic membrane and the bottom of pocket 111 with reflection coefficient R6. The light transmission along the optical path in the sample configuration can be written:

Ts=R1*R2*Tfluid*R3

Where Tfluid represents the optical transmission through the fluid and * indicates multiplication. The light transmission along the optical path in the reference configuration can be written:

Tr=R4*Treference*R5*R6

The optical density or OD of the fluid with respect to a reference fluid is proportional to the logarithm of the ratio Treference/Tfluid, or OD~log 10(Treference/Tfluid)

The quantity X=log 10(Tr/Ts) is most directly calculated from measurements of the optical transmission along the optical path in the sample (Ts) and reference (Tr) configurations. Substituting the expressions for Tr and Ts, X can be written as:

$$X = \log 10(Tr/Ts)$$
$$= \log 10(Treference/Tfluid) +$$
$$\log 10((R4*R5*R6)/(R1*R2*R3))$$

Figure 7:
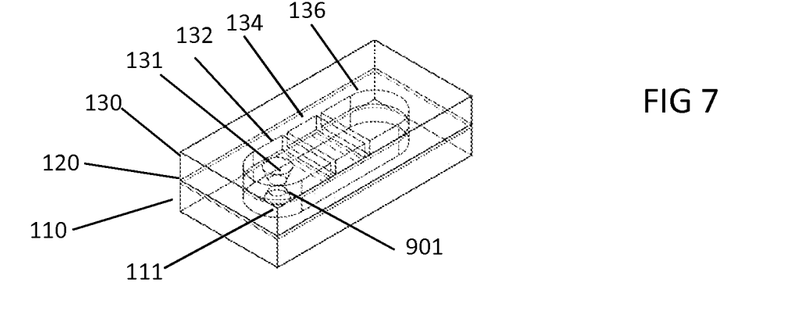
FIG. 7 shows an isometric view of a substantially planar embodiment with shorter optical path length through the fluid.
Figure 8:
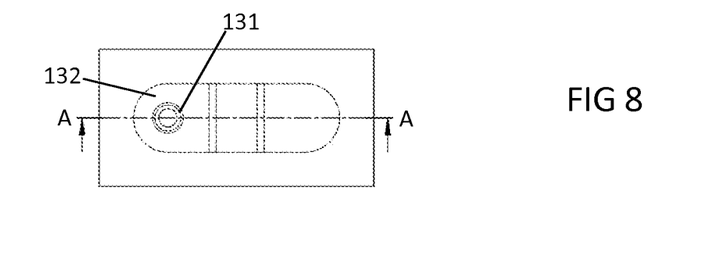
FIG. 8 is a top view of FIG. 7.
Figure 9:
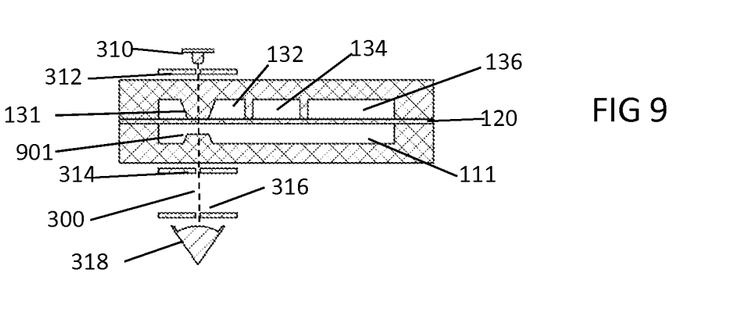
FIG. 9 is a section view along the line A-A in FIG. 8.

From this equation, it can be seen that the terms involving the reflection coefficients, appear as an additive error to the quantity log 10(Treference/Tfluid). For the most precise determination of the optical density, these terms should be corrected for by determining the reflection coefficients and estimating the optical density from the quantity Y=X−log 10((R4'*R5'*R6')/(R1'*R2'*R3'))

Where R1', R2', R3', R4', R5', and R6' are estimates of the reflection coefficients. For the case where the island 131 and the layer 110 are made from the same material, R1=R6, so the problem simplifies to estimating R2, R3, R4, and R5. For the case where the reference fluid and fluid in pocket 111 have the same refractive index, R3=R4 and R2=R5, which eliminates the additive offset since in this case Y=X It can also be preferable to reduce, or in general to change the optical path length through the fluid without changing the overall volume of the pocket 111. This was accomplished by including a second island 901 in pocket 111 that intersected the optical path 300 with height such that the optical path through the fluid was shorter than if the island were not there. This is shown in FIGS. 7-9 where FIG. 7 is an isometric view, FIG. 8 is a top view and FIG. 9 is a section view of FIG. 8 along the section line A-A. FIG. 9 also adds the optical elements analogous to FIG. 3. It should be understood that when the optical transmission was measured without the fluid when a pressurized fluid was introduced in pocket 132 that the deflected membrane analogous to FIG. 6 contacted the second island 901 of rigid material. The second island 901 was circular in shape in a preferred embodiment, but can be any shape, preferably smooth with an optional draft. The diameter of the second island in a preferred embodiment was 0.2 inches but can be 0.01 inches to 3 inches. The height of the island 901 measured from the bottom of pocket 111 was 0.04 inches but can be 0 inches to 3 inches. In particular it is to be noted that a height of the second island 901 of 0 inches corresponds to not having the second island 901.

Incorporation of the second island 901 into pocket 111 means that the range of fluid volumes in the pocket 111 over which the device can be configured in the sample configuration and the reference configuration is larger. The lower limit of the volume range is approximately determined by the minimum volume required for the membrane under pocket 132 to contact the surface of the island 131 when the membrane under pocket 136 is fully deflected and touches the bottom of pocket 111, or otherwise reaches its maximum deflection for a pressure introduced to pocket 136. The upper limit of the volume range is approximately determined by the minimum volume where the membrane under pocket 132 cannot be deflected to touch the top of the second island 901 for a selected pressure introduced into pocket 132. In addition, for sufficient pressures introduced into pocket 132 there is a physical limitation where the fluid displaced from under pocket 132 has fully deflected the membrane under pocket 136 up to contact the top surface of pocket 136. In this condition, further displacement of fluid so that the membrane can contact the top of island 901 is no longer possible. With the second island 901, the upper limit of the volume range is higher than without the island because a smaller volume of fluid needs to be displaced before the membrane touches the top of the second island 901.

A cylindrical probe embodiment of the invention is shown in FIGS. 10-14. The embodiment posses six fold rotational symmetry about the central axis. It should be noted that six fold rotational symmetry is not essential and 4-fold, 3-fold, 2-fold, or other symmetry, or no symmetry is contemplated.

Figures 10, 11:
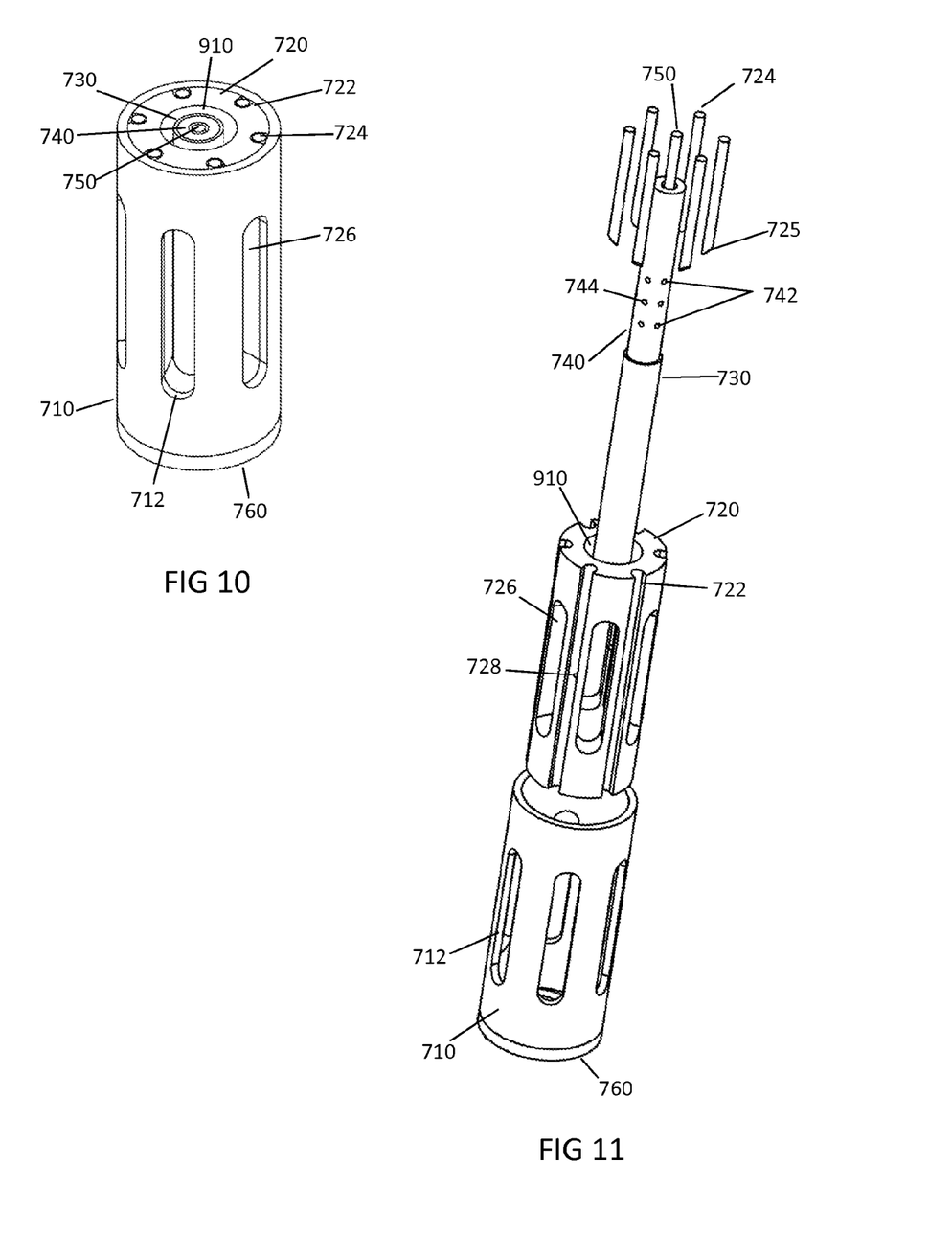
FIG. 10 is an isometric view of the bottom portion of a cylindrical probe embodiment.
FIG. 11 is an exploded view of FIG. 10.

As shown in the isometric view of FIG. 10 and exploded view of FIG. 11, the embodiment comprises a cylindrical outer shell 710 with six apertures 712; a fiber carrier 720, with six grooves 722, six fluid apertures 726, and six optical windows 728; a cylindrical membrane 730; a central tube 740 with 12 pneumatic apertures 742 and 6 optical windows 744; collection optical fibers 724; an excitation optical fiber 750; and an end cap 760.

Referring to FIG. 10 and FIG. 11 in more detail, the cylindrical outer shell 710, fiber carrier 720, end cap 760, and optical windows 728 are joined together such that the six grooves 722 are isolated from the space 910, and the space surrounding the probe. Joining methods are known in the art and may include using adhesives, epoxies, welding, soldering, or brazing, or other joining methods. The central tube 740, and end cap 760 are joined together such that air cannot enter the central tube 740 from the end joined to the end cap 760. The cylindrical membrane is joined to the central tube above and below the pneumatic apertures 742 such that the center of the central tube is isolated from the space 910 beyond the outer radial surface of the cylindrical membrane 730. Joining methods for the cylindrical membrane and central tube may include adhesives, mechanical compression, or other joining method to seal the membrane 730 to the central tube 740.

Referring to FIG. 10 and FIG. 11 in still more detail, the cylindrical outer shell 710 in a preferred embodiment can have an outer diameter of approximately 0.5 inch or 0.1 inches to 3 inches and an inner diameter of approximately 0.47 inches or 0.1 inches to 3 inches. The outer diameter of the fiber carrier 720 in a preferred embodiment can be approximately 0.47 inches or 0.1 to 3 inches, and the grooves 722 in a preferred embodiment can be 0.05 inches wide or 0.01 inches to 0.3 inches wide, and 0.05 inches deep or 0.01 inches to 0.3 inches deep. The inner diameter of the fiber carrier 720 in a preferred embodiment can be 0.22 inches or 0.1 inches to 3 inches. The outer diameter of the central tube 740 in a preferred embodiment can be 0.125 inches or 0.1 to 3 inches and the inner diameter of the central tube in a preferred embodiment can be 0.059 inches or 0.01 inches to 3 inches. The spacing between the pneumatic apertures 742 in a preferred embodiment can be 0.2 inches or 0.05 inches to 10 inches. The apertures 712 in a preferred embodiment can be approximately 0.1 inches wide or 0.01 inches to 1 inch wide, and 0.5 inches long, or 0.01 inches to 10 inches long. The excitation optical fiber 750 in a preferred embodiment may be 0.04 inches in diameter or 0.004 inches to 0.2 inches. The collection optical fibers 724 in a preferred embodiment can be 0.04 inches in diameter or 0.004 inches to 0.2 inches.

Referring to FIG. 10 and FIG. 11 in still more detail, the outer shell 710, fiber carrier 720, central tube 740, and end cap 760 may be made of stainless steel, aluminum, ceramic, plastic, or other rigid material. The cylindrical membrane 730 may be made of silicone, urethane, copolyester-ethers, or other substantially transparent elastomer. The optical fibers 724 and 750 may be made of glass, plastic, or other material.

It should be understood that FIGS. 10-14 only show the bottom portion of a cylindrical probe and that extension of the probe to the appropriate length and the addition of means to illuminate optical fibers and measure collected light should be apparent to one of ordinary skill in the art. In addition, it should be recognized that the space between the outside of the central tube 740 and the inside of the fiber carrier 720 is preferentially eliminated in the upper portion of the cylindrical probe that is not shown in FIGS. 10-14.

For the purposes of this description, a fluid to be characterized is introduced into the space 910 between the inner surface of the fiber carrier 720 and the outer surface of the cylindrical membrane 730. This fluid enters the space 910 through apertures 712 and 726 when the probe is submerged in the fluid.

Figure 12:
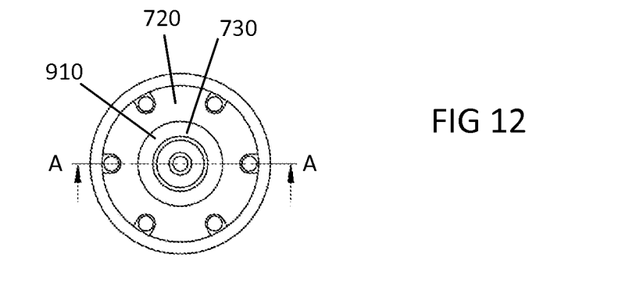
FIG. 12 is a top view of FIG. 10.
Figure 13:
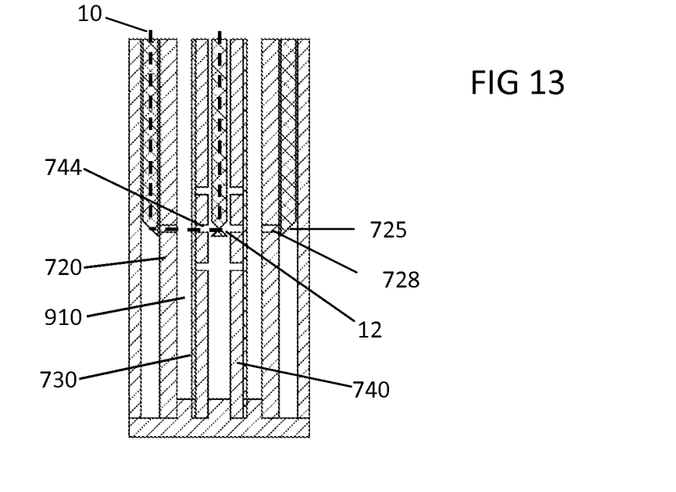
FIG. 13 is a section view along the line A-A in FIG. 12 where the cylindrical probe embodiment is configured to measure a sample transmission.
Figure 14:
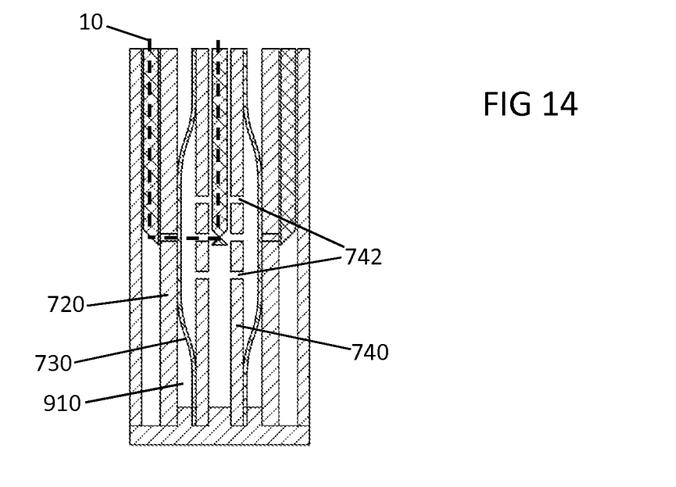
FIG. 14 is a section view along the line A-A in FIG. 12 where the cylindrical probe embodiment is configured to measure a reference transmission.

A top view of the cylindrical probe embodiment is shown in FIG. 12 and cross sectional views along the line A-A in FIG. 12 are shown in FIG. 13 and FIG. 14. In FIG. 13, the cylindrical probe embodiment is configured to measure the optical transmission through a fluid introduced in the space 910 between the inner surface of the fiber carrier 720 and the outer surface of the cylindrical membrane 730. By applying, with means obvious to one of ordinary skill in the art, a pneumatic pressure less than or equal to the hydrostatic pressure in the space 910, through the central tube 740, the cylindrical membrane 730 contracts to contact the central tube 740. An optical path 10 is indicated by the dashed line. The optical path 10 starts from the top of the central optical fiber, is directed radially by a conical prism 12, or other means, passes through an optical window 744 in the central tube, passes through the membrane 730, through fluid in the space 910, through the optical window 728 in the fiber carrier 720, reflected into a collection fiber 724, by a prism cut 725 in the collection fiber, or other means.

In FIG. 14, the cylindrical probe embodiment is configured to measure the optical transmission without the fluid for the reference measurement. By applying, with means obvious to one of ordinary skill in the art, a pneumatic pressure sufficient to bring the cylindrical membrane 730 in contact with the inner surface of the fiber carrier 720, the fluid is displaced from the optical path 10.

The cylindrical membrane can be fabricated by those of ordinary skill in the art. Examples of suitable membranes would be long transparent balloons with diameter smaller than the diameter of the central rod. The cylindrical membrane is bonded to the central rod above the uppermost pneumatic aperture 742 and also below the lowest pneumatic aperture 742 to form a region between these bonds that can expand outward when pneumatic pressure is applied to the central rod.

It should be recognized that other configurations are contemplated, including ones where the central rod is not concentric with the inner surface of the fiber carrier. In such a configuration, the optical path lengths through the fluid are different, which could be used for characterizing fluids with a potentially wide range of optical density. For measuring fluids with high optical density, a shorter path length can be advantageous for improved signal to noise or linearity.

It should also be recognized that a circular cross section of the probe is not essential and that other cross sections such as an elliptical cross section or in general any cross section that forms a closed contour are contemplated.

Example 1

A method for measuring the optical density in a fluid using the embodiment depicted in FIGS. 1-9.
1. Introduce the fluid to be characterized into the pocket 111. The volume of fluid should be in a range such that when configured to measure the sample as shown in FIG. 5, the membrane under pocket 132 contacts the island 131, and when configured to measure the reference as shown in FIG. 6, the membrane contacts the bottom of pocket 111, or for an embodiment with a second island 901 of rigid material in pocket 111, contacts the top of the island 901.
2. Configure the device to measure the fluid in pocket 111 by pressurizing pocket 136 with a deflecting fluid (gas or liquid). After the membrane has deformed to contact the island 131 of rigid material in pocket 132, measure the quantity of light transmitted through the optical path. Label this quantity Ts.
3. Configure the device to measure the transmission without the fluid in the pocket 111 by pressurizing the pocket 132 with a reference fluid (liquid or gas). After the membrane has deformed to contact the bottom surface of pocket 111, or the top surface of an island 901, measure the quantity of light transmitted through the optical path. Label this quantity Tr.
4. Compute the optical density $$OD = (\text{scale factor}) * (10 * \log 10(Tr/Ts) + (\text{correction factor}))$$

Where (scale factor) is chosen to scale the optical density to a reference optical path length through the sample and (correction factor) is chosen to correct for the difference in reflection between the elastic membrane and the fluid to be characterized and between the elastic membrane and the reference fluid; and the difference in reflection between the fluid to be characterized and the island 131 and between the reference fluid and the island 131.

Example 2

Online optical density monitoring of a microbial fermentation in a microbioreactor device using the inventive concept.

A miniature bioreactor was fabricated to implement the inventive concept, with similar in structure to the embodiment depicted in FIGS. 1-9. References made to structures in FIGS. 1-9 refer to analogous structures in the fabricated bioreactor device of this example.

The volume of pocket 111 was approximately 1 mL. An inlet channel and outlet channel to pocket 111 terminated in septa so fluid could be introduced using a syringe to puncture a septa and inject the fluid. Displaced air was removed by puncturing the septa of the outlet channel.

The pocket 134 was connected to a vacuum source through a conduit to a vacuum source. The deflecting fluid and reference fluid were both a gas mixture, with similar physical properties to air. Pocket 132 was connected through a conduit to a first 3-way solenoid valve that could connect pocket 132 to either a volume with the gas mixture maintained at a pressure of approximately 3 psig or a vent to the surrounding environment at 0 psig. Pocket 136 was similarly connected via a second conduit to a second 3-way solenoid valve that could connect pocket 136 to the gas mixture at 3 psig, or vent to the surrounding atmosphere at 0 psig.

To operate the bioreactor device, approximately 1 mL of fluid with microbial cells was introduced into pocket 111 through the inlet channel and septa using a syringe and needle. The device was maintained at 37 C. to support the growth of the microbial cells. As the microbial cells multiplied, the optical density of the fluid increased. This increase was measured using the inventive concept.

The membrane was configured to be in the sample position by configuring the two 3-way solenoid switches to connect pocket 132 to vent and pocket 136 to the gas mixture at 3 psig. In this configuration, the light source, a red light emitting diode 310 (LED) was activated by applying a current with mean value of 15 mA and sinusoidal peak to peak variation of approximately 30 mA and frequency of approximately 7 kHz. The light from the LED was directed along an optical path that passed vertically through a first aperture 312 and through the island 131, through the deflected elastomer membrane 120, through the fluid with microbial cells, through the bottom of the device layer 110, through a second aperture 314. Below the second aperture was a prism that reflected the transmitted light 90 degrees. The transmitted light then passed through a third aperture 316 to a silicon photodiode and amplifier circuit represented by 318. The amplifier circuit had a transimpedence gain that selectively amplified frequencies from approximately 1 kHz to 15 kHz. The voltage signal from the amplifier that was proportional to the transmitted light was sampled by an analog to digital converter. The signal was further processed using a lock-in detection algorithm, known in the art, to quantify the quantity of light from the LED that reached the photodiode. This quantity was recorded as Ts. The LED was then deactivated.

The membrane was then configured to be in a reference position by configuring the two 3-way solenoid switches to connect pocket 136 to vent and pocket 132 to the gas mixture at 3 psig. In this configuration, the light from the LED was directed along an optical path that passed vertically through a first aperture 312 and through the island 131, through the gas mixture at 3 psig, through the deflected elastomer membrane 120, through the bottom of the device layer 110, through a second aperture 314. Below the second aperture was a prism that reflected the transmitted light 90 degrees. The transmitted light then passed through a third aperture 316 to a silicon photodiode and amplifier circuit represented by 318. The voltage signal from the amplifier that was proportional to the transmitted light was sampled by an analog to digital converter. The signal was further processed using a lock-in detection algorithm, known in the art, to quantify the quantity of light from the LED that reached the photodiode. This quantity was recorded as Tr. The LED was then deactivated.

The optical density was then calculated as $OD = A*10*\log 10(Tr/Ts) + B$, where for simplicity $A=1$ and $B=0$.

Figure 15:
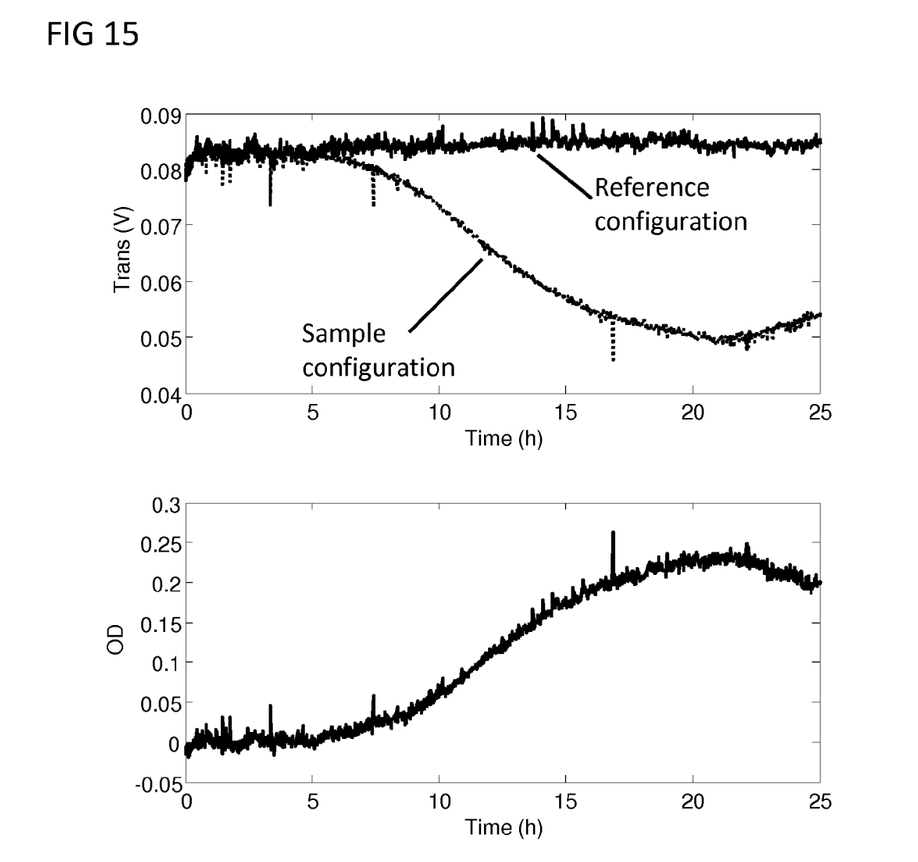
FIG. 15 is a data plot of optical transmission measurements through two configurations of an optical path and the calculated optical density.

The measurement process was repeated approximately every minute for 25 hours. The resulting data is shown in FIG. 15 where according to the labels of the figure, the transmitted light in the sample configuration and the reference configuration are shown in the upper plot and the computed optical density in the lower plot.

Figure 16:
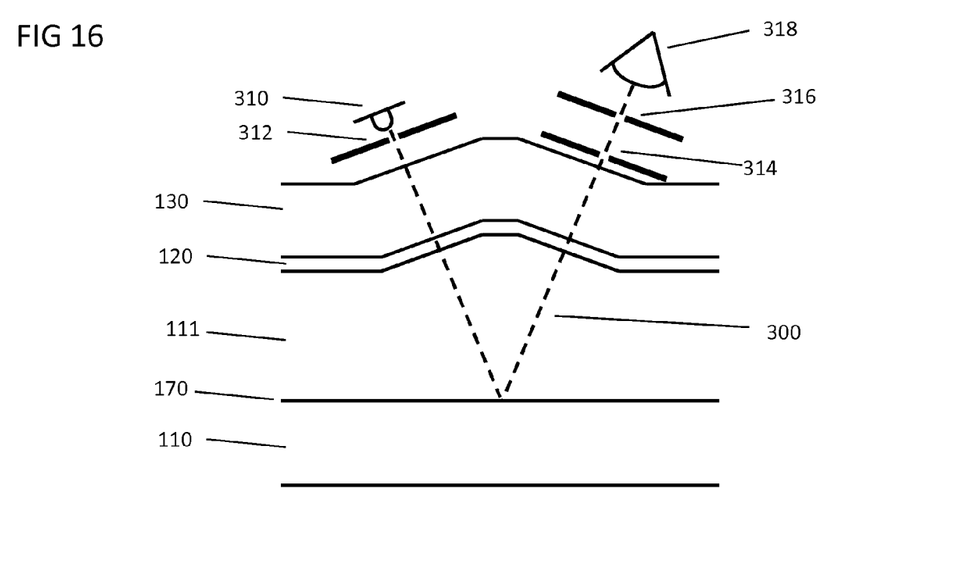
FIG. 16 is a schematic cross section view of an embodiment where a light source and light detector are on the same side configured to measure a sample transmission.
Figure 17:
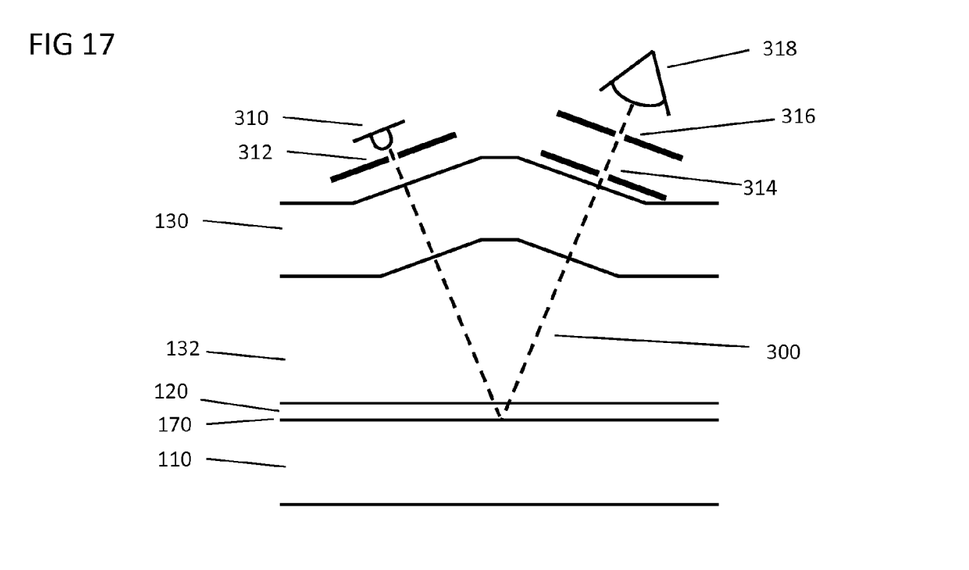
FIG. 17 is a schematic cross section view of an embodiment where a light source and light detector are on the same side configured to measure a reference transmission.

FIG. 16 and FIG. 17 depict a schematic cross section of a reflective embodiment where a light source and light detector are on the same side of the apparatus and where the optical path changes direction at the reflective surface 170. Labeled structures are analogous to those labelled in FIG. 3.

In more detail, FIG. 16 shows the reflective embodiment configured to measure a sample transmission where the membrane 120 is deflected to contact the bottom of layer 130 and the fluid is in the region 111, below the membrane 120. The optical path originates at the light source 310, passes through the first aperture 312, the layer 130, the membrane 120, the fluid in region 111, reflects off the interface 170, passes through the fluid, the membrane 120, the layer 130, the second aperture 314, the third aperture 318, and ends at the detector 318.

In more detail, FIG. 17 shows the reflective embodiment configured to measure a reference transmission. In this case, the optical path originates at the light source 310, passes through the first aperture 312, the layer 130, a reference fluid in region 111, the membrane 120, reflects off the interface 170, passes through the membrane 120, the reference fluid, the layer 130, the second aperture 314, the third aperture 318, and ends at the detector 318.

It should be clear to one of ordinary skill in the art that there are many possible methods to measure the quantity of light transmitted through the optical path. This includes methods using different light sources such as light emitting diodes, lasers, thermal light sources, or other light sources. It also includes methods using different detectors such as photodiodes, thermal detectors, and other detectors. There are also many signal amplification and processing techniques available such as using a lock-in amplification technique, where the light source is modulated at a certain frequency, f, and a photoreceiver that preferably detects light modulated at the frequency, f.

DEFINITIONS

A deformable portion of an elastic membrane refers an area of elastic membrane that is not bonded to a surface.

Fluid refers to a substance that conforms to the shape of its container and includes liquids and gasses, and also liquids with suspended solid particles.

Reference fluid refers to a liquid or gas used to deflect a portion of an elastic membrane wherein the optical path from a light source to a light detector passes through the reference fluid.

Deflecting fluid refers to a liquid or gas used to deflect a portion of an elastic membrane.

Optical path refers to a path traversed by light.

Fluid sample refers to the fluid to be characterized.

The fluid to be characterized is also referred to as fluid, without qualification.

A substantially closed surface refers to a closed surface with the allowance for openings such as an inlet or outlet.

An elastomer membrane substantially contacting a surface refers to the condition where any substance between the elastomer membrane and the surface is sufficiently thin such that any further reduction of the substance between the elastomer membrane and surface would not change the measured transmission along the optical path by more than 1 percent.

Thus, specific compositions and methods of optical density measurement have been disclosed. It should be apparent, however, to those skilled in the art that many more modifications besides those already described are possible without departing from the inventive concepts herein. The inventive subject matter, therefore, is not to be restricted except in the spirit of the disclosure.

Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Having thus described the invention, what is claimed as new and secured by Letters Patent is:

1. An apparatus for measuring the optical density of a fluid comprising:
   a light source;
   a light detector;
   an elastic membrane;
   a first deformable portion of the elastic membrane with a first side fluidically isolated from a second side that is in contact with the fluid;
   a first surface facing the second side of the first deformable portion of the elastic membrane with at least a portion of the first surface in contact with the fluid;
   a second surface facing the first side of the first deformable portion of the elastic membrane; and
   a reconfigurable optical path from the light source to the light detector that passes through the fluid in at least one configuration of the reconfigurable optical path;
   wherein:
      the optical path length through the fluid is determined by the position of the first deformable portion of the elastic membrane relative to the first surface;
      in a first configuration of the reconfigurable optical path the elastic membrane substantially contacts the second surface and the fluid is included in the reconfigurable optical path; and
      in a second configuration of the reconfigurable optical path the elastic membrane substantially contacts the first surface and the fluid is substantially excluded from the reconfigurable optical path.

2. The apparatus of claim 1 wherein the first deformable portion of the elastic membrane and the first surface are transparent to the light from the light source.

3. The apparatus of claim 1 wherein one or more of the first deformable portion of the elastic membrane and the first surface reflects the light from the light source.

4. The apparatus of claim 1 wherein the first surface and the first deformable portion of the elastic membrane are substantially planar.

5. The apparatus of claim 1 wherein a cross section of the first deformable portion of the elastic membrane on a section plane forms a closed contour.

6. The apparatus of claim 1 further comprising one or more aperture(s) wherein the reconfigurable optical path passes through the aperture(s).

7. The apparatus of claim 1 further comprising:
   a first substantially closed surface defining a first volume, wherein a portion of the first substantially closed surface comprises the first side of the first deformable portion of the elastic membrane; and
   a conduit to the first substantially closed surface.

8. The apparatus of claim 7 further comprising:
   a first source of a reference fluid at a first pressure;
   a second source of a reference fluid at a second pressure; and
   a valve selectively connecting the conduit to the first substantially closed surface to the first source at the first pressure, or to the second source at the second pressure.

9. The apparatus of claim 8 wherein the first pressure is sufficiently different from the hydrostatic pressure of the fluid wherein the first deformable portion of the elastic membrane substantially contacts the second surface in a first position when the conduit to the first substantially closed surface is connected to the first source at the first pressure; and where the second pressure is sufficiently different from the hydrostatic pressure of the fluid wherein the first deformable portion of the elastic membrane substantially contacts the first surface in a second position when the conduit to the first substantially closed surface is connected to the second source at the second pressure.

10. The apparatus of claim 7 further comprising:
    a second deformable portion of the elastic membrane with a first side fluidically isolated from a second side that is in contact with the fluid;
    a second substantially closed surface defining a second volume, wherein a portion of the second substantially closed surface comprises the first side of the second deformable portion of the elastic membrane;
    a conduit to the second substantially closed surface;
    a third substantially closed surface defining a third volume, wherein a portion of the third substantially closed surface comprises the second side of the first deformable portion of the elastic membrane and the second side of the second deformable portion of the elastic membrane and the first surface; and
    a conduit to the third substantially closed surface.

11. The apparatus of claim 10 further comprising:
    a third deformable portion of the elastic membrane with a first side fluidically isolated from a second side that is in contact with the fluid;
    a fourth substantially closed surface defining a fourth volume, wherein a portion of the fourth substantially closed surface comprises the first side of the third deformable portion of the elastic membrane;
    a conduit to the fourth substantially closed surface;
    the third substantially closed surface further comprising the second side of the third deformable portion of the elastic membrane; and
    a source of vacuum pressure connected to the conduit to the fourth substantially closed surface.

12. A method to measure optical density of a fluid comprising the steps of:
    a) configuring a first configuration of a reconfigurable optical path from a light source to a light detector that includes a first optical path length through the fluid defined by a first surface and a second side of a deformable portion of an elastic membrane, wherein the deformable portion of the elastic membrane is deflected in a first position where a first side of the deformable portion of the elastic membrane substantially contacts a second surface;
b) activating the light source and the light detector;
c) measuring the quantity of light transmission, T1, through the reconfigurable optical path, configured in the first configuration, from the light source to the light detector that includes the first optical path length through the fluid;
d) configuring a second configuration of the reconfigurable optical path from the light source to the light detector that substantially excludes the fluid, wherein the deformable portion of the elastic membrane is deflected in a second position where the second side of the deformable portion of the elastic membrane substantially contacts the first surface; and
e) measuring the quantity of light transmission, T2, through the reconfigurable optical path, configured in the second configuration, from the light source to the light detector that substantially excludes the fluid.

13. The method of claim 12 comprising the additional step of
a) computing the optical density using the formula:

$$\text{optical\_density} = A*\log 10(T2/T1) + B, \text{ where } A \text{ and } B \text{ are constants.}$$

* * * * *